(12) United States Patent
Biederman et al.

(10) Patent No.: US 11,038,555 B2
(45) Date of Patent: Jun. 15, 2021

(54) SYSTEMS AND METHODS FOR ENABLING NFC COMMUNICATIONS WITH A WEARABLE BIOSENSOR

(71) Applicant: Verily Life Sciences LLC, South San Francisco, CA (US)

(72) Inventors: William Biederman, San Francisco, CA (US); Anil Kumar Ram Rakhyani, Union City, CA (US); Louis Jung, Foster City, CA (US); Stephen O'Driscoll, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 16/528,798

(22) Filed: Aug. 1, 2019

(65) Prior Publication Data

US 2020/0044695 A1 Feb. 6, 2020

Related U.S. Application Data

(60) Provisional application No. 62/714,799, filed on Aug. 6, 2018.

(51) Int. Cl.
*H04B 5/00* (2006.01)
*H01Q 1/27* (2006.01)
(Continued)

(52) U.S. Cl.
CPC ....... *H04B 5/0043* (2013.01); *A61B 5/14532* (2013.01); *H01Q 1/273* (2013.01); *H01Q 7/00* (2013.01); *H01Q 11/08* (2013.01)

(58) Field of Classification Search
CPC .. H04B 5/0043; A61B 5/14532; H01Q 1/273; H01Q 7/00; H01Q 11/08
See application file for complete search history.

(56) References Cited

U.S. PATENT DOCUMENTS 7,031,945 B1 4/2006 Donner
8,798,541 B1 8/2014 Scott
(Continued)

FOREIGN PATENT DOCUMENTS

CA 2553507 11/2009
CN 101193671 6/2008
(Continued)

OTHER PUBLICATIONS

"NFC Antenna : Add-on for your NFC Patch", <https://flomio.com/shop/readers/nfc-antenna/> downloaded Oct. 14, 2019.
(Continued)

*Primary Examiner* — Mohamed Barakat
(74) *Attorney, Agent, or Firm* — Kilpatrick Townsend & Stockton LLP

(57) ABSTRACT

One example system for enabling NFC communications with a wearable biosensor includes a biosensor applicator including a housing defining a cavity configured to receive and physically couple to a biosensor device, and to apply the biosensor device to a wearer; a first applicator coil antenna physically coupled to the housing and defined within a first plane; and a second applicator coil antenna physically coupled to the housing and defined within a second plane substantially parallel to and different from the first plane, the second applicator coil antenna positioned coaxially with respect to the first applicator coil antenna, wherein the first applicator coil antenna is configured to wirelessly receive electromagnetic ("EM") energy from a transmitter coil antenna of a remote device and provide at least a first portion of the received EM energy to the second coil antenna; and a biosensor device including a biosensor coil antenna defined within a third plane substantially parallel to and different than the first and second planes; a wireless receiver electrically coupled to the biosensor coil antenna; wherein
(Continued)

the biosensor device is physically coupled to the biosensor applicator and positioned within the cavity; wherein the biosensor coil antenna is positioned and oriented substantially coaxially with respect to the second applicator coil antenna, and wherein the second applicator coil antenna is configured to receive EM energy from the first applicator coil antenna and wirelessly transmit at least a second portion of the received EM energy to the biosensor coil antenna.

31 Claims, 10 Drawing Sheets

(51) Int. Cl.
*A61B 5/145* (2006.01)
*H01Q 11/08* (2006.01)
*H01Q 7/00* (2006.01)

(56) References Cited

U.S. PATENT DOCUMENTS

| | | | |
|---|---|---|---|
| 8,947,041 | B2 | 2/2015 | Cook et al. |
| 9,110,897 | B2 | 8/2015 | Park et al. |
| 9,246,555 | B2 | 1/2016 | Griffin et al. |
| 9,901,293 | B2 | 2/2018 | Dehennis et al. |
| 9,967,001 | B2 | 5/2018 | Biederman |
| 2003/0012566 | A1 | 1/2003 | Kindaichi |
| 2003/0050009 | A1 | 3/2003 | Kurisko et al. |
| 2006/0173260 | A1 | 8/2006 | Gaoni et al. |
| 2007/0008139 | A1 | 1/2007 | Saarisalo et al. |
| 2008/0116847 | A1 | 5/2008 | Loke et al. |
| 2010/0045425 | A1 | 2/2010 | Chivallier |
| 2010/0148723 | A1 | 6/2010 | Cook et al. |
| 2010/0292556 | A1 | 11/2010 | Golden |
| 2011/0022411 | A1 | 1/2011 | Hjelm et al. |
| 2011/0046548 | A1 | 2/2011 | Sakata et al. |
| 2011/0221590 | A1 | 9/2011 | Baker et al. |
| 2012/0003933 | A1 | 1/2012 | Baker et al. |
| 2012/0028575 | A1 | 2/2012 | Chen et al. |
| 2013/0029596 | A1 | 1/2013 | Preston et al. |
| 2013/0069753 | A1 | 3/2013 | Kurs et al. |
| 2013/0217979 | A1 | 8/2013 | Blackadar et al. |
| 2013/0274629 | A1* | 10/2013 | Duesterhoft ......... A61B 5/0022 600/573 |
| 2014/0138432 | A1 | 5/2014 | Park et al. |
| 2014/0184422 | A1 | 7/2014 | Mensinger et al. |
| 2014/0273821 | A1 | 9/2014 | Miller et al. |
| 2014/0313052 | A1 | 10/2014 | Yarger et al. |
| 2015/0018643 | A1 | 1/2015 | Cole et al. |
| 2015/0054621 | A1 | 2/2015 | Lin et al. |
| 2015/0075770 | A1 | 3/2015 | Fripp et al. |
| 2015/0343144 | A1 | 12/2015 | Altschul et al. |
| 2016/0015267 | A1 | 1/2016 | Bernstein et al. |
| 2016/0183854 | A1* | 6/2016 | Lee .................... A61B 5/14514 600/347 |
| 2016/0242685 | A1 | 8/2016 | DeHennis et al. |
| 2016/0310663 | A1* | 10/2016 | Dantsker ............. G16H 20/17 |
| 2016/0331232 | A1 | 11/2016 | Love et al. |
| 2016/0331283 | A1 | 11/2016 | Rao et al. |
| 2017/0040818 | A1 | 2/2017 | Kong et al. |
| 2017/0047636 | A1 | 2/2017 | Lee et al. |
| 2017/0079587 | A1* | 3/2017 | Fougere ............. A61B 5/14507 |
| 2017/0173262 | A1 | 6/2017 | Veltz |
| 2017/0185284 | A1 | 6/2017 | Bhavaraju et al. |
| 2017/0337461 | A1* | 11/2017 | Jesme ................ G06K 19/0723 |
| 2018/0026678 | A1 | 1/2018 | Biederman |
| 2018/0192514 | A1* | 7/2018 | Seo ...................... H05K 3/1283 |
| 2018/0199813 | A1 | 7/2018 | Love et al. |
| 2018/0234133 | A1 | 8/2018 | Biederman |

FOREIGN PATENT DOCUMENTS

| | | |
|---|---|---|
| CN | 102144239 | 8/2011 |
| CN | 204576485 | 8/2015 |
| CN | 105686807 | 6/2016 |
| WO | 2013063634 | 5/2013 |
| WO | 2016081244 | 6/2016 |
| WO | 2018022235 | 2/2018 |

OTHER PUBLICATIONS

"NFC Patch Kit : Extend your NFC reach", <https://flomio.com/shop/nfc-readers/nfc-patch-kit/> downloaded Oct. 14, 2019.
U.S. Appl. No. 15/218,587, Advisory Action, dated Oct. 5, 2017, 3 pages.
U.S. Appl. No. 15/218,587, Final Office Action, dated Jul. 24, 2017, 16 pages.
U.S. Appl. No. 15/218,587, Non-Final Office Action, dated Jan. 12, 2017, 13 pages.
U.S. Appl. No. 15/218,587, Notice of Allowance, dated Jan. 10, 2018, 8 pages.
U.S. Appl. No. 15/945,286, Advisory Action, dated Feb. 7, 2019, 3 pages.
U.S. Appl. No. 15/945,286, Final Office Action, dated Nov. 2, 2018, 19 pages.
U.S. Appl. No. 15/945,286, Non Final Office Action, dated Jun. 4, 2018, 17 Pages.
U.S. Appl. No. 16/030,383, Advisory Action, dated Feb. 19, 2020, 3 pages.
U.S. Appl. No. 16/030,383, Advisory Action, dated Apr. 12, 2019, 5 pages.
U.S. Appl. No. 16/030,383, Final Office Action, dated Nov. 19, 2019, 25 pages.
U.S. Appl. No. 16/030,383, Final Office Action, dated Feb. 8, 2019, 26 pages.
U.S. Appl. No. 16/030,383, Non-Final Office Action, dated Oct. 9, 2018, 22 pages.
U.S. Appl. No. 16/030,383, Non-Final Office Action, dated Jul. 12, 2019, 24 pages.
Chinese Application No. CN201780046360.7, Notice of Decision to Grant, dated Jul. 3, 2020, 2 pages.
Chinese Application No. CN201780046360.7, Office Action, dated Nov. 11, 2019, 9 pages.
Jara et al., "Communication Protocol for Enabling Continuous Monitoring of Elderly People through Near Field Communications", Interacting with Computers, May 15, 2013, 2 pages.
International Application No. PCT/US2017/039380, International Preliminary Report on Patentability, dated Feb. 7, 2019, 8 pages.
International Application No. PCT/US2017/039380, International Search Report and Written Opinion, dated Sep. 7, 2017, 11 pages.
International Application No. PCT/US2019/044789, International Search Report and Written Opinion, dated Nov. 7, 2019, 12 pages.

\* cited by examiner

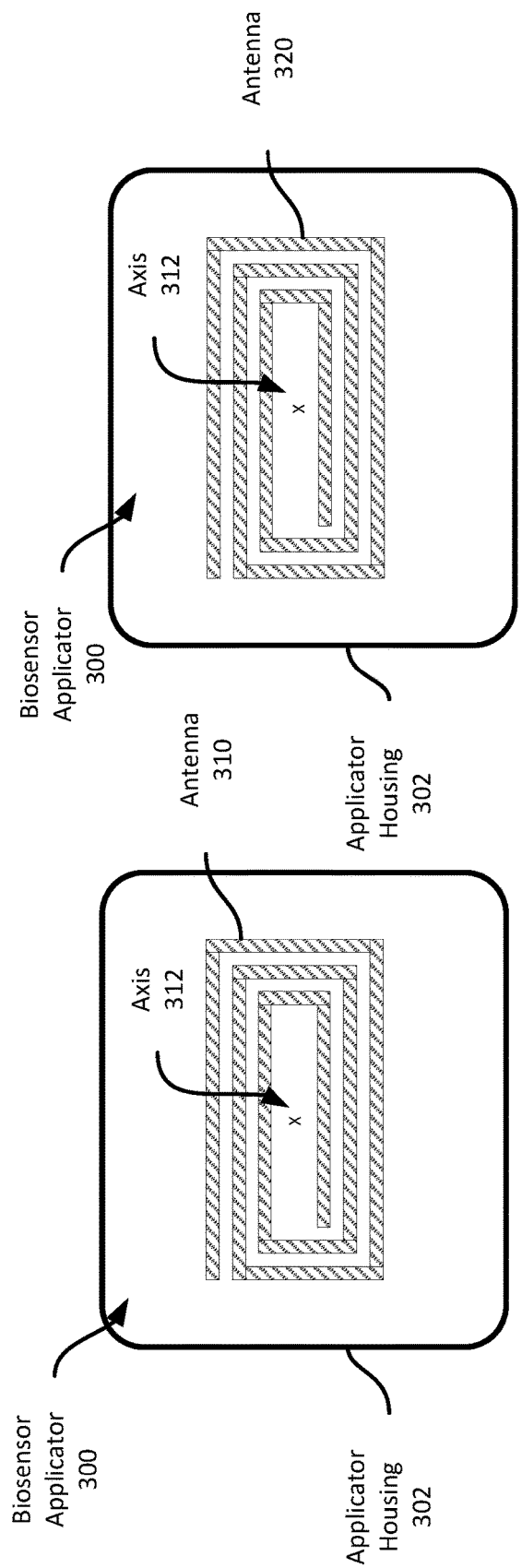
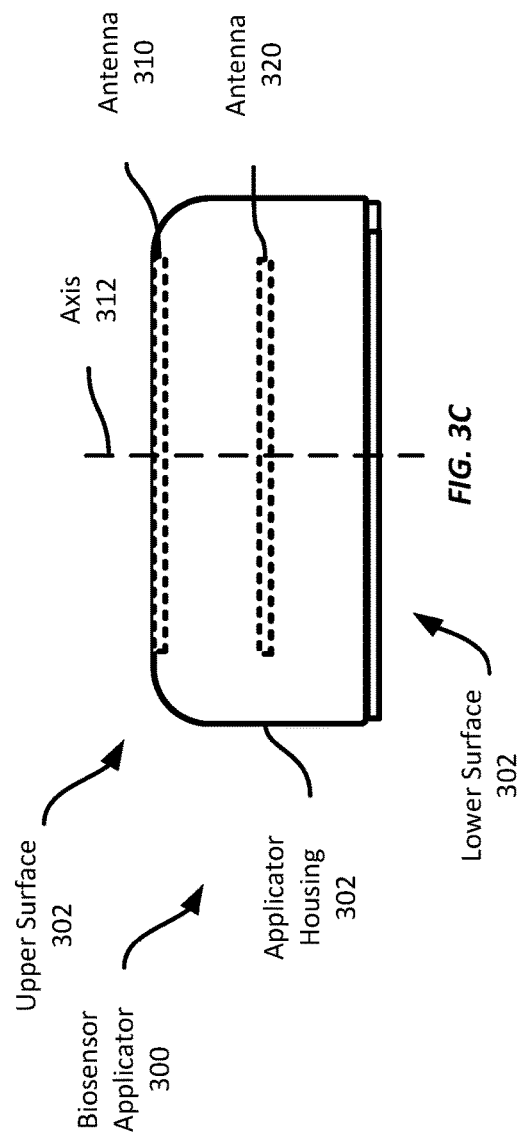

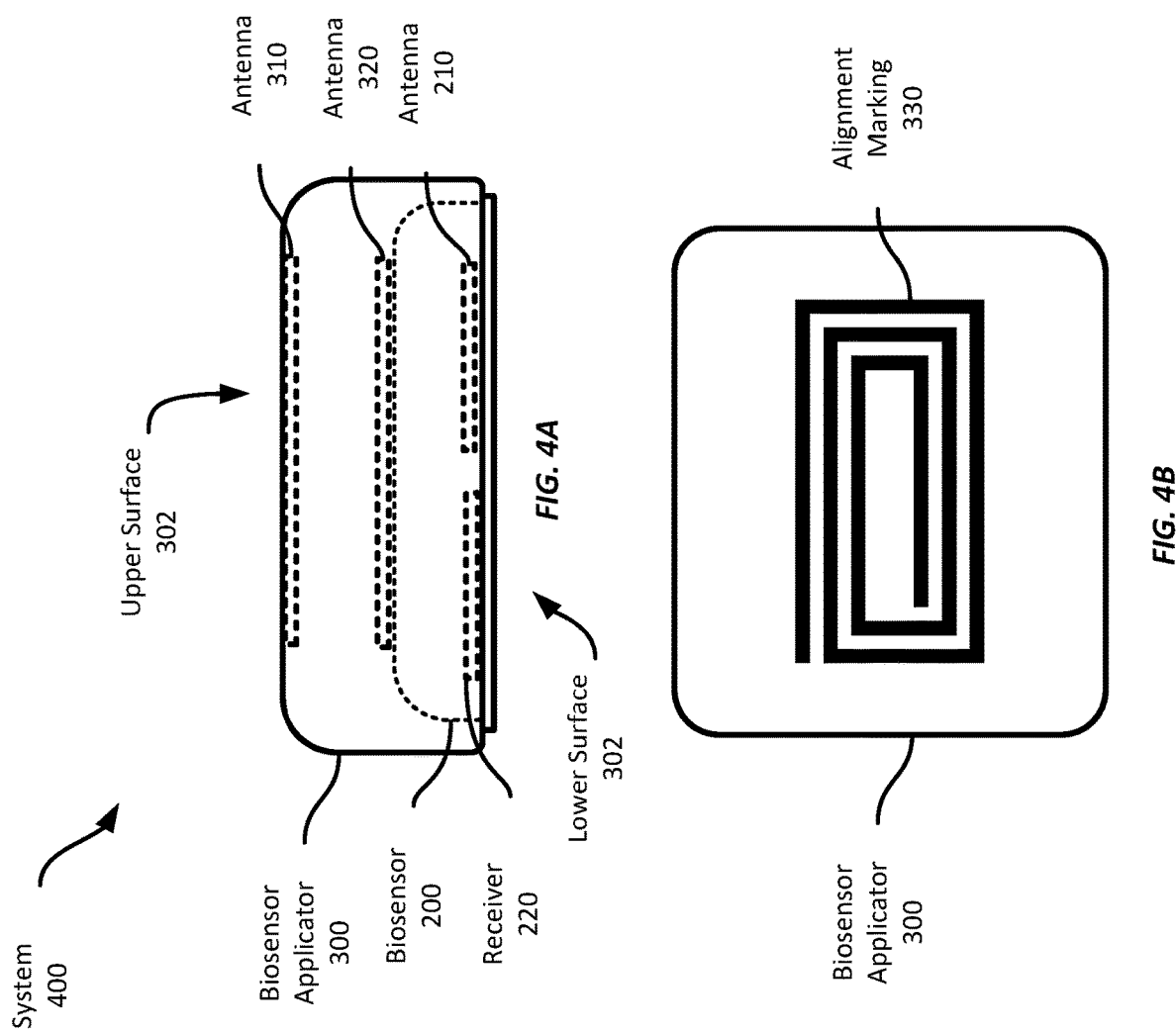

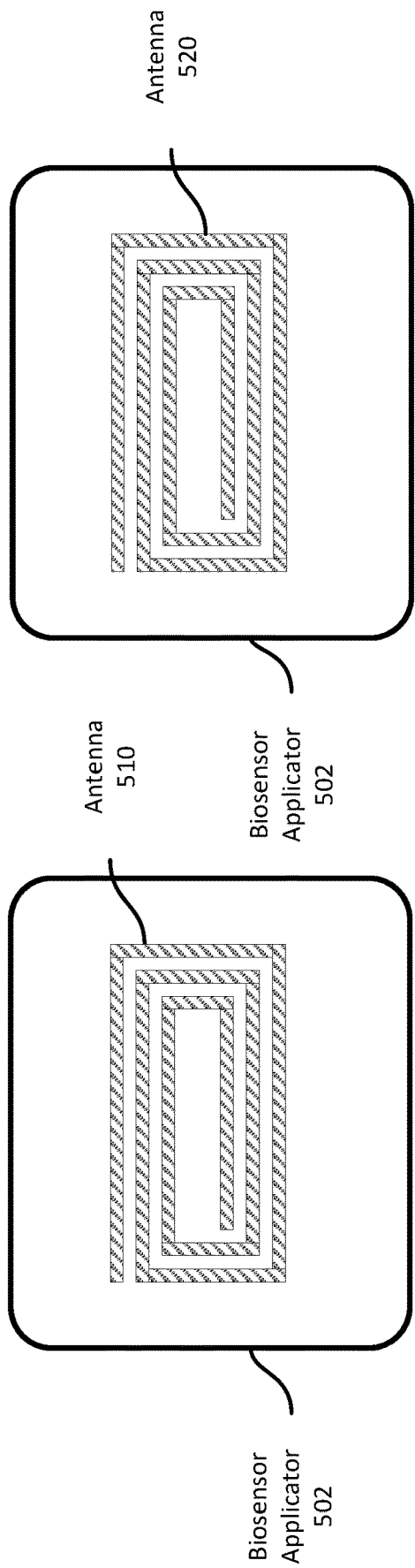
FIG. 5A
FIG. 5B
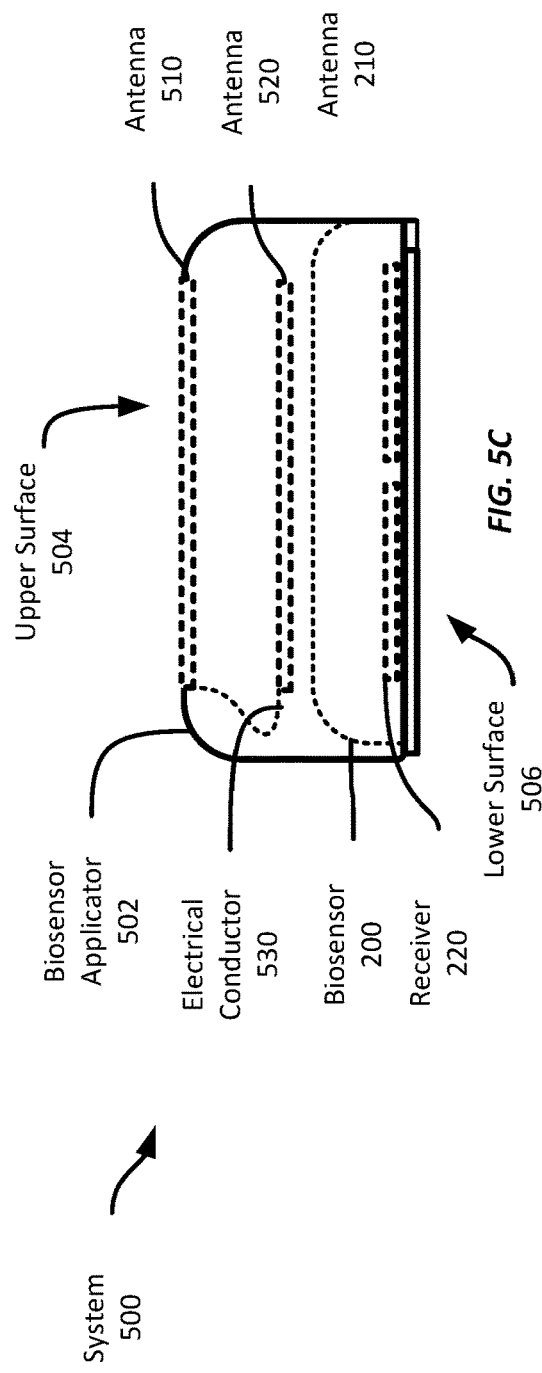
FIG. 5C

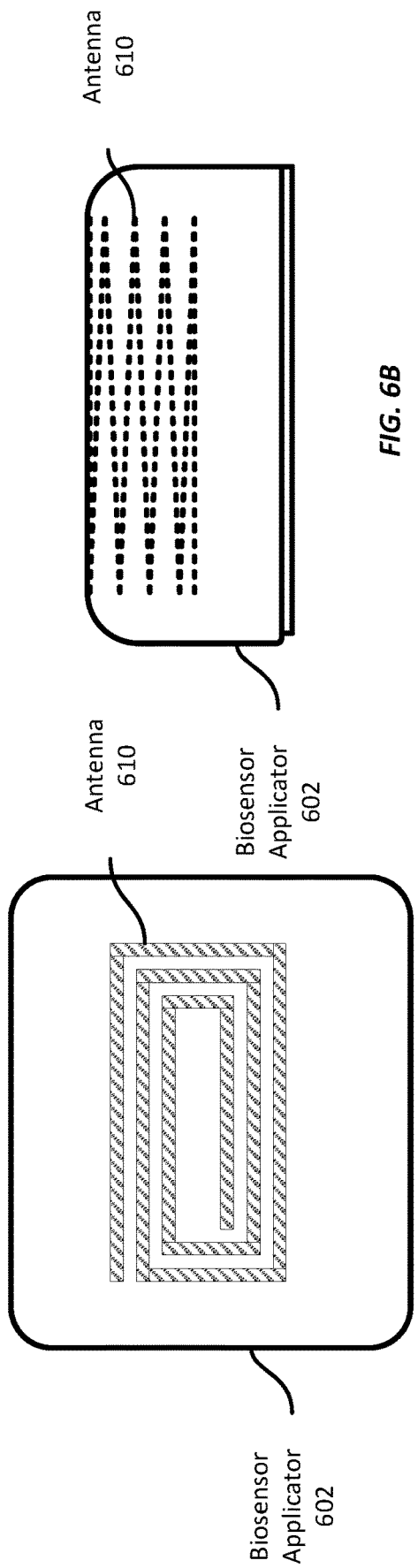
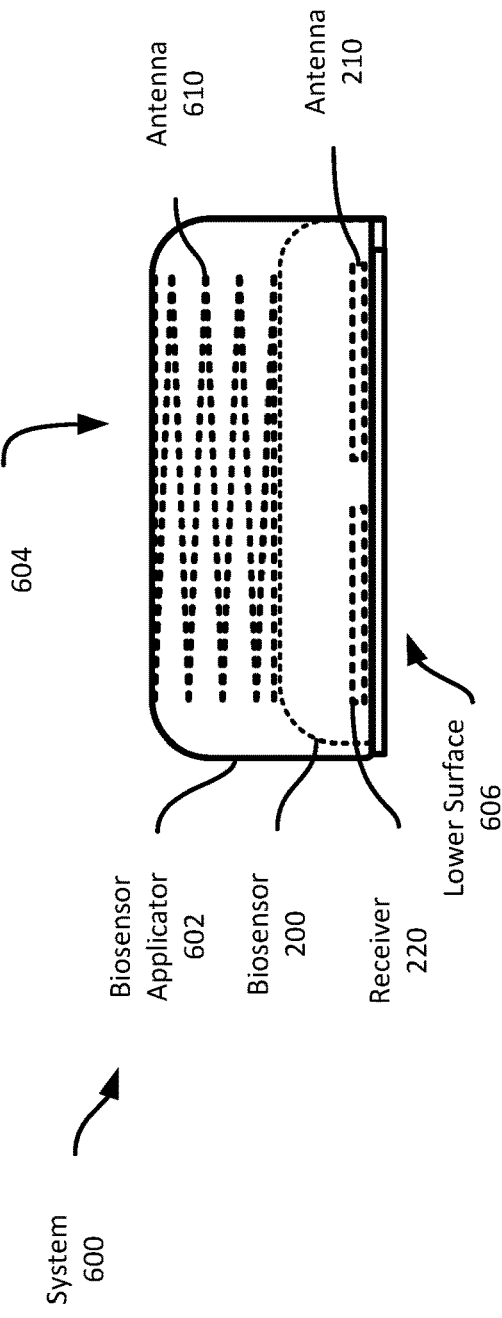

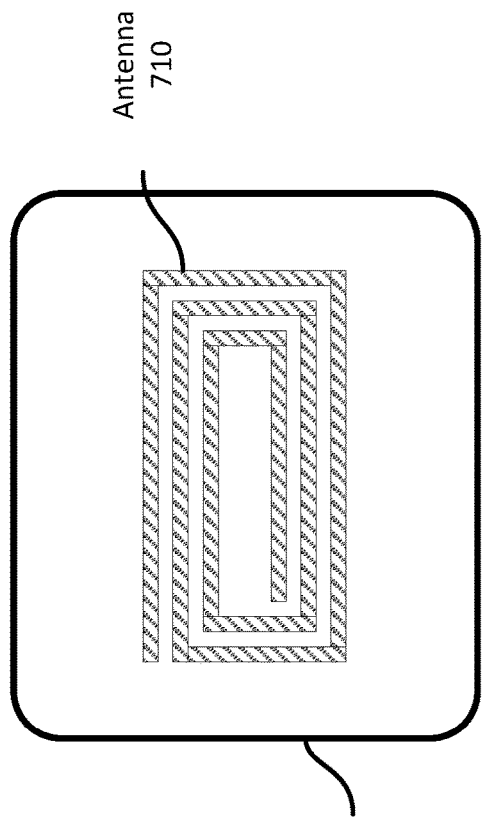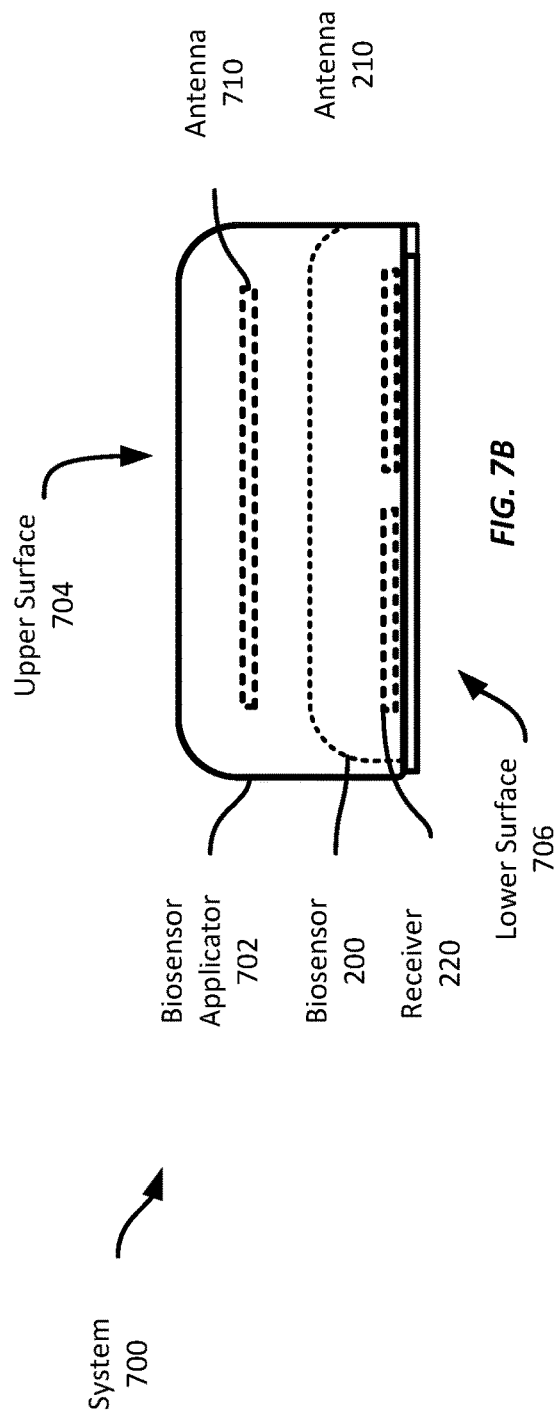

SYSTEMS AND METHODS FOR ENABLING NFC COMMUNICATIONS WITH A WEARABLE BIOSENSOR

CROSS REFERENCE TO RELATED APPLICATION

This application claims the benefit of U.S. Application No. 62/714,799, filed Aug. 6, 2018, titled "Systems And Methods For Enabling NFC Communications With A Wearable Biosensor," which is incorporated herein by reference in its entirety.

FIELD

The present application generally relates to wireless communications between electronic devices, and more particularly relates to systems and methods for enabling NFC communications with a wearable biosensor

BACKGROUND

Computing devices may communicate with other computing devices using wireless communications techniques, such as Bluetooth ("BT"), BT low-energy ("BLE"), WiFi, near-field communications ("NFC"), etc. Depending on the type of wireless communication technique employed, the computing devices may be located at great distances from each other, or may need to be brought into close proximity. In addition, different wireless communication techniques may require different levels of power consumption to enable effective wireless communication. Thus, different wireless communication techniques may be suited for different types of computing devices or use cases than others.

SUMMARY

Various examples are described for systems and methods for enabling NFC communications with a wearable biosensor. For example, one system includes a biosensor applicator comprising: a housing defining a cavity configured to receive and physically couple to a biosensor device, and to apply the biosensor device to a wearer; a first applicator coil antenna physically coupled to the housing and defined within a first plane; and a second applicator coil antenna physically coupled to the housing and defined within a second plane substantially parallel to and different from the first plane, the second applicator coil antenna positioned coaxially with respect to the first applicator coil antenna, wherein the first applicator coil antenna is configured to wirelessly receive electromagnetic ("EM") energy from a transmitter coil antenna of a remote device and provide at least a first portion of the received EM energy to the second coil antenna; and a biosensor device comprising: a biosensor coil antenna defined within a third plane substantially parallel to and different than the first and second planes; a wireless receiver electrically coupled to the biosensor coil antenna; wherein the biosensor device is physically coupled to the biosensor applicator and positioned within the cavity; wherein the biosensor coil antenna is positioned and oriented substantially coaxially with respect to the second applicator coil antenna, and wherein the second applicator coil antenna is configured to receive EM energy from the first applicator coil antenna and wirelessly transmit at least a second portion of the received EM energy to the biosensor coil antenna One example biosensor applicator includes a biosensor applicator housing configured to receive and physically couple to a biosensor device, the biosensor applicator configured to apply the biosensor device to a wearer; a first coil antenna physically coupled to the biosensor applicator housing; and a second coil antenna physically coupled to the biosensor applicator housing, the second coil antenna located distant from the first coil antenna and substantially co-axially aligned with the first coil antenna, and wherein the first coil antenna is configured to: wirelessly receive electromagnetic ("EM") energy from a transmitter coil antenna; and provide at least a portion of the received EM energy to the second coil antenna.

A further example biosensor applicator includes a biosensor applicator housing configured to receive and physically couple to a biosensor device, the biosensor applicator configured to apply the biosensor device to a wearer; a first coil antenna; wherein the first coil antenna is configured to: wirelessly receive electromagnetic ("EM") energy from a transmitter coil antenna, and provide at least a portion of the received EM energy to a biosensor coil antenna of a biosensor device.

One example method includes generating, using an electronic device, an alternating electromagnetic field ("EMF"), the electronic device comprising a wireless transmitter and a transmitter coil antenna, the wireless transmitter electrically coupled to the wireless transmitter; receiving, by a first coil antenna of a biosensor applicator, energy from the alternating EMF, wherein the biosensor applicator comprises: the first coil antenna; and a second coil antenna, the second coil antenna located distant from and substantially co-axially aligned with the first coil antenna; transmitting, by the first coil antenna, energy received from the alternating EMF to the second coil antenna; transmitting, by the second coil antenna, energy received from the first coil antenna to a biosensor coil antenna of a biosensor device, wherein the biosensor device comprises the biosensor coil antenna and a wireless receiver, the biosensor coil antenna electrically coupled to the wireless receiver.

A further example method includes generating, using an electronic device, an alternating electromagnetic field ("EMF"), the electronic device comprising a wireless transmitter and a transmitter coil antenna electrically coupled to the wireless transmitter; receiving, by a first coil antenna of a biosensor applicator, energy from the alternating EMF, the biosensor applicator comprising the first coil antenna; and transmitting, by the first coil antenna to a biosensor coil antenna, the energy received from the alternating EMF.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 3A-3C show an example wearable biosensor applicator;

FIGS. 4A-4B show an example system for enabling NFC communications with a wearable biosensor;

FIGS. 5A-5C show an example wearable biosensor applicator and an example system for enabling NFC communications with a wearable biosensor;

FIGS. 6A-6C show an example wearable biosensor applicator and an example system for enabling NFC communications with a wearable biosensor;

FIGS. 7A-7B show an example wearable biosensor applicator and an example system for enabling NFC communications with a wearable biosensor;

DETAILED DESCRIPTION

Examples are described herein in the context of systems and methods for enabling NFC communications with a wearable biosensor. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Wearable biosensors may be used for a variety of different reasons and may be used to sense many different physiological characteristics of a wearer. For example, referring to FIG. 1, a diabetic may wear a continuous glucose monitor ("CGM") 120 to monitor her glucose levels and determine whether she needs a dose of insulin or needs to consume some food. To apply the CGM 120, the wearer purchases a new CGM 120 and removes it from the package. The CGM 120 is installed within a CGM applicator 130, which is a device that helps the user apply the CGM 120 to her body, such as by puncturing her skin to enable the CGM's sensor wire to be inserted beneath her skin. Before she applies the CGM 120, however, she first activates the CGM 120.

Figure 1:
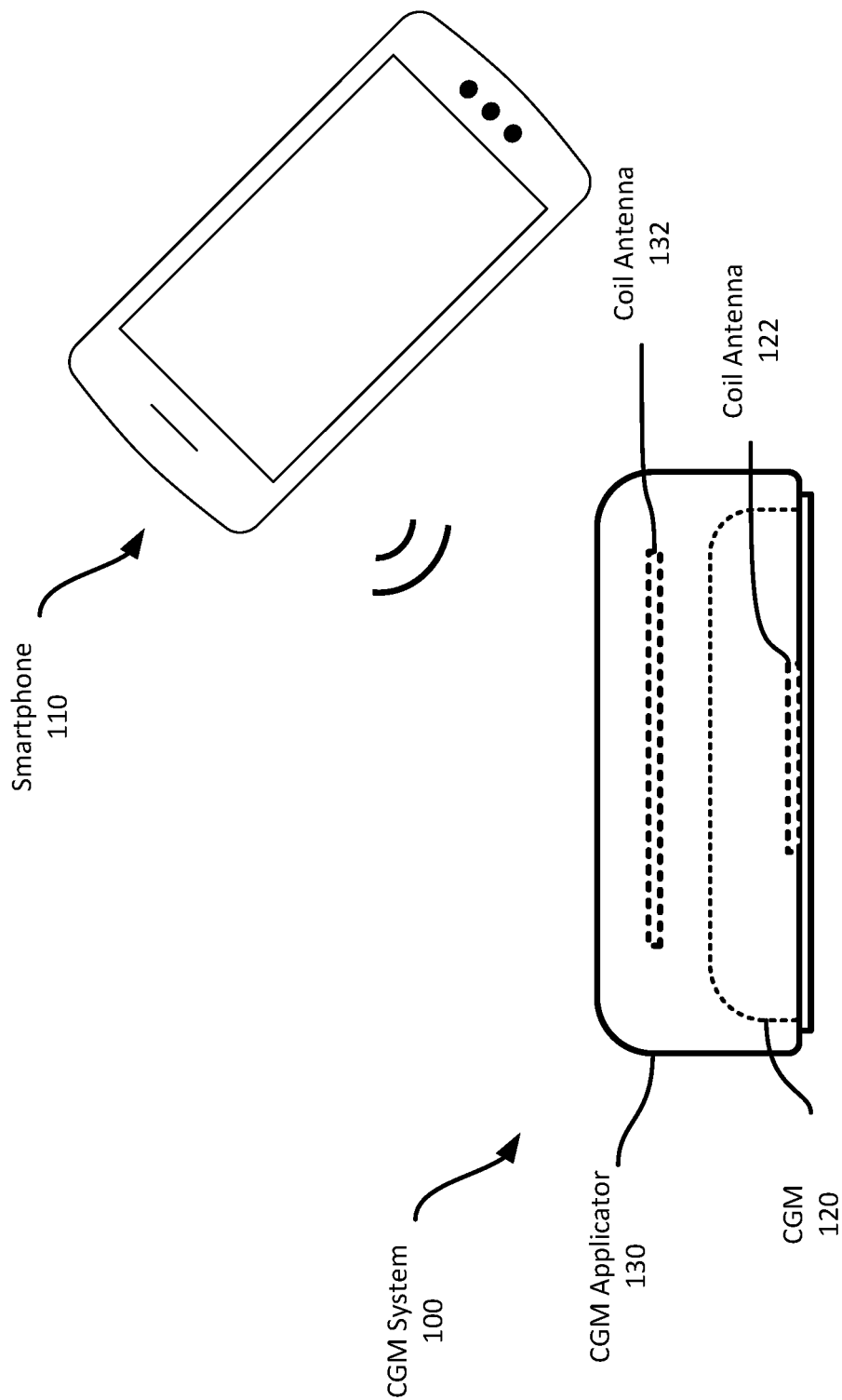
FIG. 1 shows an example system for enabling NFC communications with a wearable biosensor.

In this example, the CGM 120 is configured to use NFC communications to communicate with the wearer's smartphone 110 (or other computing device) as shown in FIG. 1. However, because the CGM 120 is installed within the CGM applicator 130, and NFC has a relatively short effective communications range, the CGM applicator 130 itself may prevent the NFC communication between the user's smartphone and the CGM 120, simply by being a physical barrier between the smartphone and the CGM 120 that prevents the two from being positioned closely enough to enable NFC communications.

To alleviate this potential problem, the CGM applicator 130 has an NFC coil antenna embedded within it. The CGM applicator's coil antenna 132 can receive NFC communications from the smartphone 110 and relay them to the CGM's NFC antenna 122. In this example, to help enable this relay functionality, the CGM applicator's coil antenna 132 is co-axially aligned with the CGM's coil antenna 122. When a varying electromagnetic field ("EMF") is applied to the CGM applicator's coil antenna 132, it energizes and is able to electromagnetically couple with the CGM's coil antenna 122, thereby transferring energy from the received EMF to the CGM's coil antenna 122 and NFC receiver.

Thus, to activate the CGM 120, the wearer launches an app on her smartphone 110 and selects an option to activate a new CGM. The app then activates the smartphone's NFC communication system and energizes its coil antenna to generate a varying EMF. Since NFC has an effective communications range on the order of a few centimeters to a few tens of centimeters, she brings her smartphone close to the new CGM system 100, which includes the CGM applicator 130 and the CGM 120. She then aligns her smartphone with a coil antenna within the CGM applicator 130, such as by visually locating the coil antenna 132 itself, or finding one or more alignment markings on the CGM applicator 130.

When she brings the smartphone 110 near the CGM applicator's coil antenna 132, i.e., she brings the smartphone 110 within the effective transmission range of the CGM applicator's coil antenna 132, the generated EMF electromagnetically couples the smartphone's coil antenna with the CGM applicator's coil antenna 132. The CGM applicator's coil antenna 132, after receiving the energy from the EMF, electromagnetically couples with the CGM's coil antenna 122 and transfers the energy to the CGM using the electromagnetic coupling.

In this example, the varying EMF field generated by the wearer's smartphone 110 includes an activation command that is propagated to the CGM 120 via the coil antennas as discussed above. After receiving the activation command, the CGM 120 activates and transmits a confirmation to the smartphone 110 using the same propagation technique, but in reverse from the CGM 120 back to the smartphone 110. Upon receiving the confirmation from the CGM 120, the app presents a notification to the wearer that the CGM 120 was successfully activated.

After receiving confirmation that the CGM 120 has been activated, the wearer then uses the CGM applicator 130 to apply the CGM 120 to her body and affix it to her skin. She then discards the CGM applicator 130, leaving the CGM 120 in place.

The CGM applicator 130 in this example enables NFC communications between the wearer's smartphone 110 (or other computing device) and the CGM's NFC receiver by providing an intermediate coil antenna to relay EMF energy to the CGM. The EMF energy may be used to send commands to the CGM or to power the CGM (or both). Thus, the CGM applicator enables NFC communications that might otherwise be prevented or degraded because the CGM applicator itself prevents the wearer's smartphone 110 from moving within effective communications range of the CGM's coil antenna 122, or otherwise interferes with communication between the two. And while the example above was in the context of a CGM and CGM applicator, any suitable biosensor device, including wearable biosensors, may be employed according to different examples. Further, and as will be discussed in more detail below, other intermediate coil configurations including multiple coils may be employed in some examples to extend the range of NFC communications between a smartphone (or other wireless computing device) and a receiving coil antenna.

This illustrative example is given to introduce the reader to the general subject matter discussed herein and the disclosure is not limited to this example. The following sections describe various additional non-limiting examples and examples of systems and methods for enabling NFC communications with a wearable biosensor.

Figure 2A:
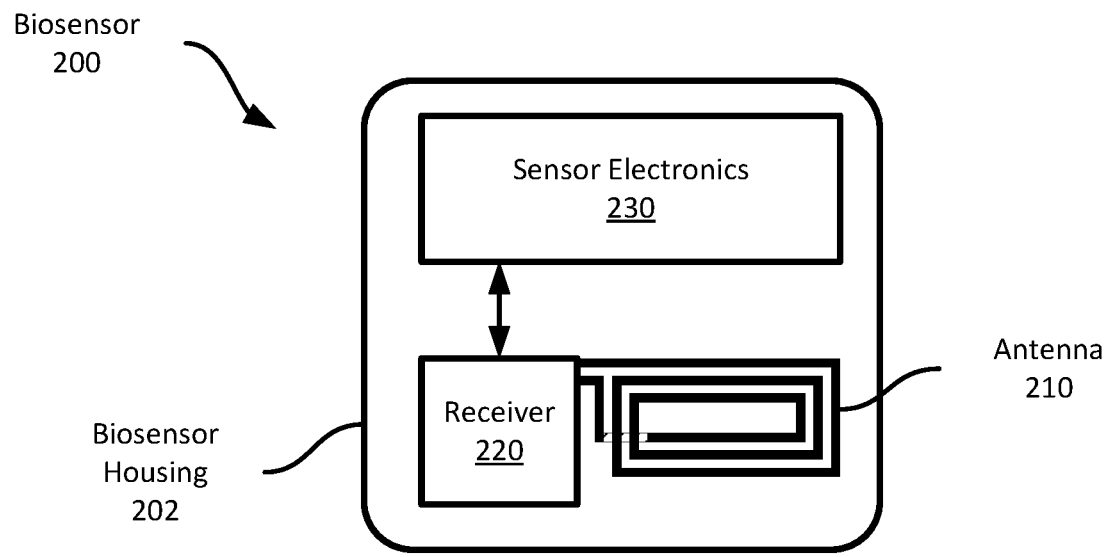
FIGS. 2A-2B show an example wearable biosensor.
Figure 2B:
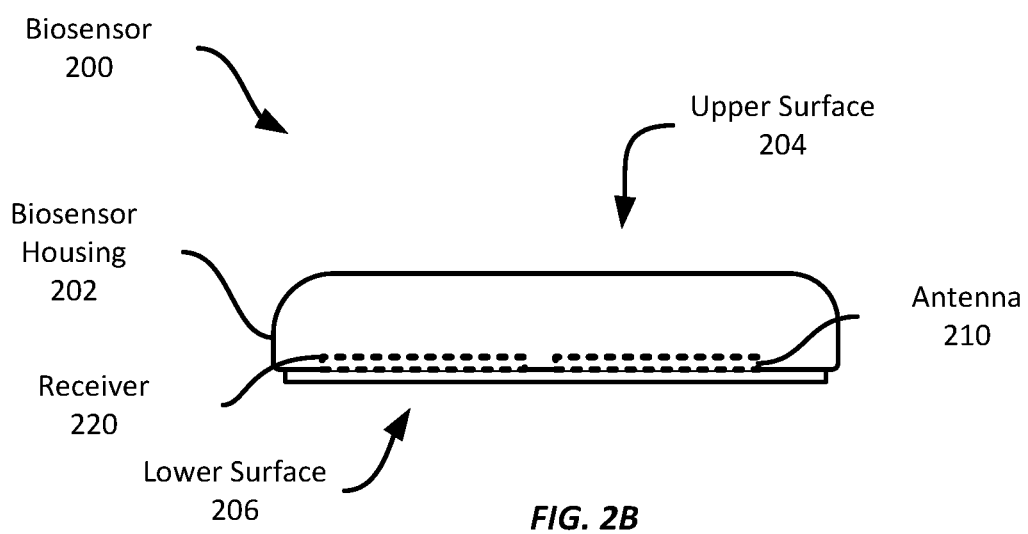

Referring now to FIGS. 2A-2B, FIG. 2A shows a top-down view of an example biosensor 200 usable with one or more systems or methods for enabling NFC communications with a wearable biosensor. The biosensor 200 includes a housing 202 inside which are sensor electronics 230, a wireless receiver 220, and a coil antenna 210. In this example, the biosensor 200 includes sensor electronics 230 that include a CGM, which includes a sensor wire to be inserted into a wearer's skin to measure glucose levels within the wearer's interstitial fluid. However, the sensor electronics 230 may include any suitable biosensor(s). For example, one or more sensors may be incorporated into the biosensor 200, including invasive or non-invasive sensors, such as analyte sensors (e.g., glucose, lactate, alcohol, etc.), blood pressure sensors, pulse sensors, blood oxygen sensors (e.g., SvO2, SpO2, etc.), galvanic skin response sensors, ultraviolet light sensors, etc.

The sensor electronics 230 may include one or more processors, memory, a battery or other power supply (e.g., photovoltaic cells), etc. The sensor electronics 230 are communicatively coupled with the wireless receiver 220 to allow communications between the wireless receiver 220 and the sensor electronics 230. Communications may include data, commands, electrical power, etc. according to different examples.

In this example, the wireless receiver 220 is part of a wireless transceiver that enables wireless communications with a remote device using the coil antenna 210; however it should be appreciated that according to different examples, the biosensor 200 may not include a wireless transceiver, but only a wireless receiver 220. The wireless receiver 220 is configured to receive NFC communications; however, any suitable short-range wireless communications protocol may be employed according to different examples. In the context of this application, "short-range" refers to implementations of communications techniques that have an effective range of a few centimeters ("cm") (e.g., less than 30 cm) without intervening physical obstructions.

The coil antenna 210 is an electrical conductor, e.g., a wire or electrical trace formed on a substrate, formed in a coil shape to enable electromagnetic coupling with another coil antenna via a varying EMF and to electromagnetically couple to the receiver 220. In this example, the coil antenna 210 substantially planar, however, example coil antennas 210 may instead be helical. In this example, the coil antenna 210 has a rectangular shape, suitable coil antennas may have any shape, including circular, ovoid, etc. Further, suitable coil antennas may be substantially planar or may extend along an axis, such as in a helical configuration.

FIG. 2B shows a side view of the biosensor 220, which illustrates the biosensor's components within the biosensor's housing 202. In this view, the receiver 220 and antenna 210 are both positioned on a common substrate on a bottom portion of the biosensor housing. The sensor electronics 230 are also physically coupled to the bottom portion of the biosensor housing 202, however, they are occluded by the receiver 220 and antenna 210 in this view. The bottom portion of the housing 202 refers to the portion of the housing 202 that will be positioned on or adjacent to the wearer's skin or clothing. It should be appreciated that the coil antenna 210 may be positioned at any suitable position within or on the biosensor housing 202. For example, the antenna 210 may be physically coupled to the top portion of the biosensor housing 202 or on an outer surface of the biosensor housing 202, e.g., the top portion of the biosensor housing 202. In such an arrangement, the coil antenna 210 may be communicatively coupled to the receiver 220 by one or more conductors, such as wires or conductive traces, e.g., conductive traces formed on the housing 202.

Referring now to FIGS. 3A-3C, FIGS. 3A-3C illustrate an example biosensor applicator 300 usable with systems and methods for enabling NFC communications with a wearable biosensor. In this example, the biosensor applicator 300 has a housing 302 and two antennas 310, 320, and is configured to accept a biosensor within the housing 302 as will be discussed in more detail with respect to FIGS. 4A-4B below.

In this example, FIG. 3A shows a top-down view of the biosensor applicator 300. In this view, a first antenna 310 of the two antennas is shown as positioned on the inner surface of an upper portion of the housing 302. Upper portion refers to the portion of the housing 302 opposite the portion of the housing 302 into which a biosensor may be inserted. While, in this example, the first antenna 310 is positioned on an inner surface of the housing 302, in some examples, the first antenna 310 may be positioned on an outer surface of the housing 302. Such a configuration may allow the wearer to more easily identify the location of the antenna 310. In this example, the antenna 310 has a substantially planar configuration, though in some examples, it may have a helical configuration.

Referring to FIG. 3B, FIG. 3B shows a top-down cross-sectional view of the interior of the biosensor applicator 300. In this view, a second antenna 320 is positioned within the interior of the housing 302 and is substantially axially aligned with the first coil antenna. As can be seen, each antenna 310, 320 is a coil around an axis running perpendicularly to the respective coil's plane. In this example, the two coils 310, 320 are positioned such that they substantially share a common central axis 312, denoted by an 'x' in FIGS. 3A-3B, and by axis 312 in FIG. 3C. Such an alignment may enable the coils to electromagnetically couple upon application of a varying EMF to one (or both) of the coils. Similar to the first antenna 310, the second antenna 320 in this example has a substantially planar configuration, though in some examples it may have a helical configuration.

It should be appreciated that while the antennas 310, 320 in this example do not have circular cross-section, in some examples, one or both of the antennas 310, 320 may have a substantially circular cross-section. In some examples, however, any suitable coil shape may be employed.

Referring now to FIG. 3C, FIG. 3C shows a side cross-section of the biosensor applicator 300. In this example, the applicator 300 does not include a conductor physically coupling the first coil antenna 310 to the second coil antenna 310; however, other examples do have such a conductor, as will be discussed in more detail below. Thus, in this example the two coil antennas 310, 320 are spaced apart by a distance of a few centimeters. In one example, however, the two coils are spaced apart by a distance of no more than twice a radius of the first or second coil. In some examples, one or both coils may not have a circular shape. In such examples, "radius" refers to a distance from the center axis 312 to an outer edge of the antenna 310, 320.

In this example, the applicator's two coil antennas 310, 320 each have a radius of substantially 4 cm; however, any suitable radius or width may be employed. It should be appreciated, however, that an effective electromagnetic coupling distance may be up to substantially twice the radius or width of an electromagnetic coil in some examples. Therefore, a size of one or more coil antennas may be selected based on a needed effective range. For example, if distance between the biosensor coil antenna 210 and the top surface of the applicator is 6 cm, a single coil antenna, e.t., first antenna 310, may have a radius of substantially 3 cm.

Alternatively, if two coil antennas are employed, smaller radii may be employed based on the positions of the coil antennas within the applicator 300.

In operation, a reader device with an NFC transmitter and coil antenna, such as the smartphone 110 shown in FIG. 1, may be brought within an effective transmission range of the biosensor applicator 300. When the reader device's NFC transmitter is activated, it generates an alternating EMF using its coil antenna, which electromagnetically couples with the first coil antenna 310. The first coil antenna 310 may then electromagnetically couple with the second coil antenna 320, effectively extending the range of the reader device's own coil antenna. Absent the first or second coil antennas 310, 320, the alternating EMF may not be able to effectively penetrate the applicator housing 302 to reach a biosensor within the applicator 300.

Referring now to FIGS. 4A-4B, FIG. 4A shows a side view of an example system 400 for enabling NFC communications with a wearable biosensor. The system 400 includes the biosensor applicator 300 shown in FIGS. 3A-3C, and the biosensor 200 shown in FIGS. 2A-2C. As can be seen, the biosensor 200 is positioned within the applicator 300, forming a monolithic system 400. The monolithic system 400 can be used to apply the biosensor 200 to a wearer's skin. For example, if the biosensor 200 is a CGM, the applicator 300 may include a needle to puncture the wearer's skin and to allow one or more CGM sensor wires to be inserted through the puncture.

As can be seen, the biosensor 200 is positioned within the applicator 300 such that the applicator's two antennas 310, 320 sit above the biosensor 200. And while the biosensor 200 is entirely disposed within the applicator in this example, in other examples, the biosensor 200 may partially protrude from the applicator 300, or it may physically couple to an outer surface of the applicator's housing 302.

In this example, the biosensor's antenna 210 is offset from the coaxially aligned antennas 310, 320 in the applicator; however, in some examples, the biosensor's antenna 210 may be coaxially aligned with the applicator's antennas 310, 320. In addition, in this example, the biosensor's antenna 210 has a smaller radius than the radii of the applicator's antennas 310, 320; however, in some examples, the biosensor's antenna 210 may have substantially the same radius or a larger radius than the applicator's antenna's 310, 320.

In this example, the first antenna 310 is positioned on an inside of the top surface of the applicator 300. Thus, when a reader device, such as a smartphone, energizes its transmission coil antenna within effective range of the first antenna 310, the first antenna 310 electromagnetically couples with the reader device's coil antenna and receives EMF energy from the reader device. The first antenna 310 then uses the received energy received to electromagnetically couple with the second antenna 320. The second antenna 320 then receives the EMF energy from the first antenna 310, and uses the received EMF energy to electromagnetically couple with the biosensor's coil antenna 210, which transfers EMF energy to the biosensor's coil antenna 210. Thus, the arrangement of antennas 210, 310, 320 in the applicator and biosensor effectively extend the range of the reader device's own transmission coil antenna, allowing the energy emitted by the reader device to effectively reach the biosensor's coil antenna 210 despite potentially being outside of an effective range of the transmission coil.

In this example, because the first antenna 310 is located on the interior of the applicator's housing, such as to protect to the first antenna 310 from damage, an alignment marking 330 is provided on the outer top surface of the applicator 300. FIG. 4B shows an example alignment marking 330 to enable a user to more easily align the reader device with the first antenna. In some examples, however, the first antenna 310 may be positioned on the outer top surface of the applicator 300, or may be embedded in the top surface and made visible, e.g., via a transparent window, and such an alignment marking 330 may not be used.

Referring now to FIGS. 5A-5C, FIGS. 5A-5C show an example system 500 for enabling NFC communications with a wearable biosensor. FIG. 5A illustrates a top-down view of a biosensor applicator 502. In this view, a first antenna 510 of the applicator's two antennas 510, 520 is shown as being positioned on the inner surface of an upper portion of the applicator 502, while a second coil antenna 520 is positioned within the interior of the applicator 502. In this example, the applicator's two antennas 510, 520 are coaxially aligned with each other, substantially as described above with respect to FIGS. 3A-3C.

In this example, unlike the example discussed above with respect to FIGS. 3A-3C, the applicator's two antennas are physically and electrically coupled by an electrical conductor 530, such as a wire or an electrical trace formed on the applicator's housing. The electrical conductor 530 enables energy received by the first antenna 510 to be transferred to the second antenna 520. Thus, rather than only employing electromagnetic coupling, the first and second antennas 510, 520 exchange energy via the electrical conductor. Thus, if a reader device is positioned within an effective range of the first antenna 510, the reader device's coil antenna will electromagnetically couple with the first antenna 510 and the conductor 530 will transfer EMF energy to the first antenna 510. The received energy will then traverse the electrical conductor 530 to the second antenna 520. It should be appreciated that the first antenna 510 will wirelessly electromagnetically couple with the second antenna 520 as well; however, the electrical conductor 530 provides a direct wired conductive pathway to transfer the energy as well. The second antenna 520 will then electromagnetically couple with the biosensor's coil antenna 210. The biosensor's coil antenna 210 may then receive any commands, data, or power transmitted by the reader device.

Thus, similar to the example shown in FIGS. 4A-4B, the applicator's two antennas 510, 520 effectively extend the range of the reader device's coil antenna. Further, the electrical conductor 530 may provide a more efficient pathway for energy transfer between the first and second coil antennas 510, 520 than a wireless electromagnetic coupling. It should be appreciated that while the coil antennas 510, 520 in this example has a substantially planar configuration, in some examples one or both may have a helical configuration.

Referring now to FIGS. 6A-6C, FIGS. 6A-6C show an example system 600 for enabling NFC communications with a wearable biosensor. FIG. 6A shows a top-down view of a biosensor applicator 602 having a coil antenna 610. In this example, the biosensor applicator 602 only has one coil antenna within its housing to electromagnetically couple with a reader device and with a biosensor's antenna 210. As can be seen in FIG. 6B, the coil antenna 610 has a helical configuration rather than being substantially planar. Thus, the coil antenna 610 is physically coupled to an inner surface of an upper portion of the applicator's housing and extends towards a bottom surface of the applicator housing along an axis. While the coil antenna 610 in this example is shown with a particular configuration having approximately five turns and a turn pitch (the axial spacing between adjacent turns) of approximately the width of the antenna's conductor, other antenna configurations may have any suitable number of turns or turn pitch.

FIG. 6C shows the system 600, including the biosensor applicator 602 with an installed biosensor 200. As can be seen in this view of the biosensor applicator 602, its coil antenna 610 extends axially towards the biosensor 200. In this example, the applicator's coil antenna 610 extends to within a few millimeters ("mm") from an upper outer surface of the biosensor 200. Such a spacing may provide a more effective electromagnetic coupling between the applicator's coil antenna 610 and the biosensor's coil antenna 210 when the applicator's coil antenna 610 is energized.

In this example, similar to the example shown in FIGS. 5A-5C, the biosensor's coil antenna 210 is not axially aligned with the applicator's antenna 610; however, such an axial alignment may not be necessary in some examples. For example, the energy emitted by the applicator's antenna 610 may be sufficient to enable electromagnetic coupling with a misaligned antenna 210. In some examples, however, the applicator's coil antenna 610 and the biosensor's coil antenna 210 may be designed to be axially aligned with the other.

Referring now to FIGS. 7A-7B, these figures show an example system 700 including a biosensor applicator 702 and a biosensor 200. In this example, the biosensor applicator 702 includes only one coil antenna 710, which is positioned within an interior portion of the biosensor applicator 702 at a location between the applicator's upper surface 704 and the biosensor's upper surface 204. Specifically, in this example, the applicator's coil antenna 710 is positioned equidistant between the applicator's upper surface 704 and the biosensor's upper surface 204. However, in some examples other positions may be employed. For example, the applicator's coil antenna 710 may be positioned equidistant between the applicator's upper surface 704 and the biosensor's coil antenna 210.

Example applicators or similar devices according to this disclosure employing only one coil antenna, similar to those employing two or more coil antennas as discussed above with respect to FIGS. 3A-5C, may effectively increase the effective range of an NFC or similar coil antenna in a reader device by providing an intermediate electromagnetic coupling between the reader device and a target device, such as a biosensor. In applications where a reader device is obstructed from moving within an effective near-field communications range of a target device, such as due to an intervening device or applicator, example arrangements of one or more intermediate coil antennas, including helical antennas, may be positioned within the intervening device or applicator to enable propagation of such near-field communications from the reader device, through the intervening device, and to the coil antenna of the target device. Such techniques may enable communications through obstacles or over distances that might otherwise impair or prevent NFC communication between a reader device and a target device.

Figure 8:
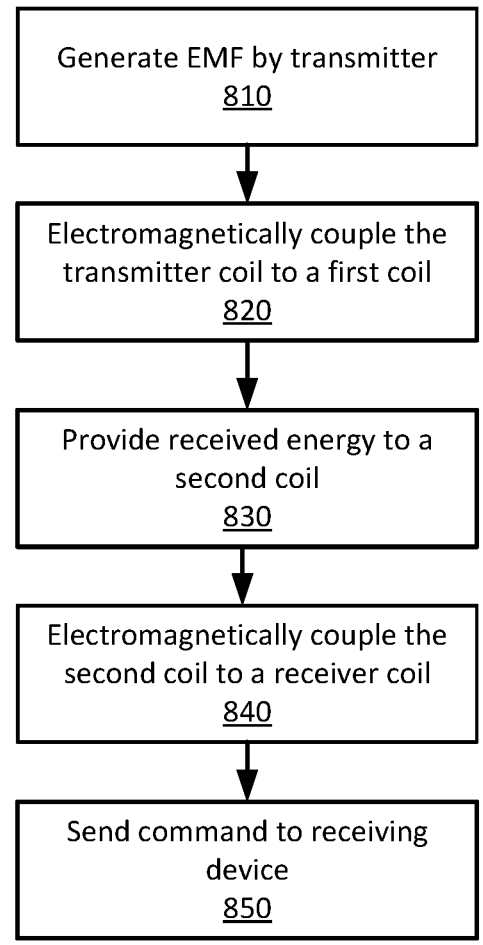
FIGS. 8-9 show example methods for enabling NFC communications with a wearable biosensor.

Referring now to FIG. 8, FIG. 8 shows an example method 800 for enabling NFC communications with a wearable biosensor. The example method 800 will be discussed with respect to the example system 400 shown in FIG. 4 and the example wireless reader device 1000 shown in FIG. 10, and described in more detail below; however any suitable system and reader device according to this disclosure may be employed.

At block 810, a reader device 1000 generates an EMF using a wireless transmitter 1012 that is electrically coupled to a coil antenna 1014. In this example, the reader device 1000 generates a varying EMF using the transmitter 1012 according to a NFC technique; however, any suitable near-field wireless communication technique may be employed.

At block 820, the reader device 1000 is brought into proximity of a device having a coil antenna. In this example, the device is a system 400 including a biosensor applicator 300 with an installed biosensor 200. The biosensor applicator 300 includes two coil antennas 310, 320. In this example, the reader device is positioned such that the first antenna 310 within the biosensor applicator 300 is within the effective range of the reader device's coil antenna 1014, such as within a few centimeters. After the reader device's coil antenna 1014 is energized by the transmitter 1012 and is generating an EMF, the reader device's coil antenna 1014 electromagnetically couples with the applicator's first antenna 310, thereby transferring energy to the first antenna 310.

At block 830, the applicator's first coil antenna 310 uses the received energy from the reader device 1000 to electromagnetically couple with the applicator's second antenna 320, thereby transferring energy to it. It should be appreciated that if the device does not include a second antenna, such as in the examples shown in FIGS. 6A-6c and 7A-7B, block 830 may be omitted. Further, if the device includes more than two antennas, block 830 may be repeated for each additional antenna, thereby propagating energy transmitted by the reader device 1000 through the successive coil antennas within the device.

At block 840, the second coil antenna 320 uses received energy from the first antenna 310 to electromagnetically couple to the biosensor's coil antenna 210. The energy received at the biosensor's coil antenna 210 is then conducted to its wireless receiver 220, where it may be used by the biosensor.

At block 850, the reader device 1000 transmits a command to the biosensor using the indirect electromagnetic coupling, provided by the applicator's first and second coil antennas 310, 320, to the biosensor's coil antenna 210. In this example, the reader device 1000 transmits an activation command to the biosensor 200. The activation command is configured to cause the biosensor to activate, which may include emerging from a sleep or pre-use mode, activating a power supply within the biosensor 200, activating one or more electronic components within the biosensor, etc. In response to the activation command, the biosensor 200 may also transmit a response to the activation command using the indirect electromagnetic coupling between the biosensor's coil antenna 210 and the reader device's coil antenna 1014. And while this example employed an activation command, it should be appreciated that any suitable command or data may be communicated using the indirect electromagnetic coupling between the reader device's coil antenna 1014 and the biosensor's coil antenna 210.

In some examples, rather than transmitting a command or data, the reader device 1000 may provide power to the biosensor 210, such as to charge a battery within the biosensor 200. In some examples, the reader device 1000 may transmit both power to charge a battery and to provide one or more commands to the biosensor.

Figure 9:
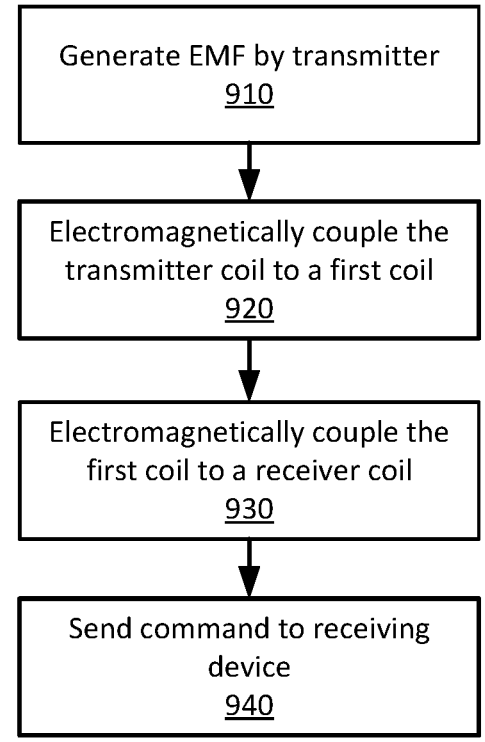

Referring now to FIG. 9, FIG. 9 shows an example method 900 for enabling NFC communications with a wearable biosensor. The method 900 will be discussed with respect to the example system 600 shown in FIGS. 6A-6C and the example reader device 1000 shown in FIG. 10, discussed in more detail below; however, any suitable device system or reader device may be employed according to different examples.

At block 910, the reader device's wireless transmitter 1012 generates an EMF using its coil antenna 1014 substantially as described above with respect to block 1010.

At block 920, the reader device's coil antenna 1014 electromagnetically couples to the applicator's coil antenna 610, substantially as discussed above with respect to block 1020.

At block 930, the applicator's coil antenna 610 electromagnetically couples to the applicator's coil antenna 610 substantially as discussed above with respect to block 1040. Thus, in contrast to the example shown in FIG. 8, this example method 900 uses only one coil within the applicator device 602; however, as discussed above with respect to block 830 of method 800, any suitable number of coil antennas may be employed.

At block 940, the reader device 1000 transmits a command to the biosensor 200 substantially as discussed above with respect to block 850.

Figure 10:
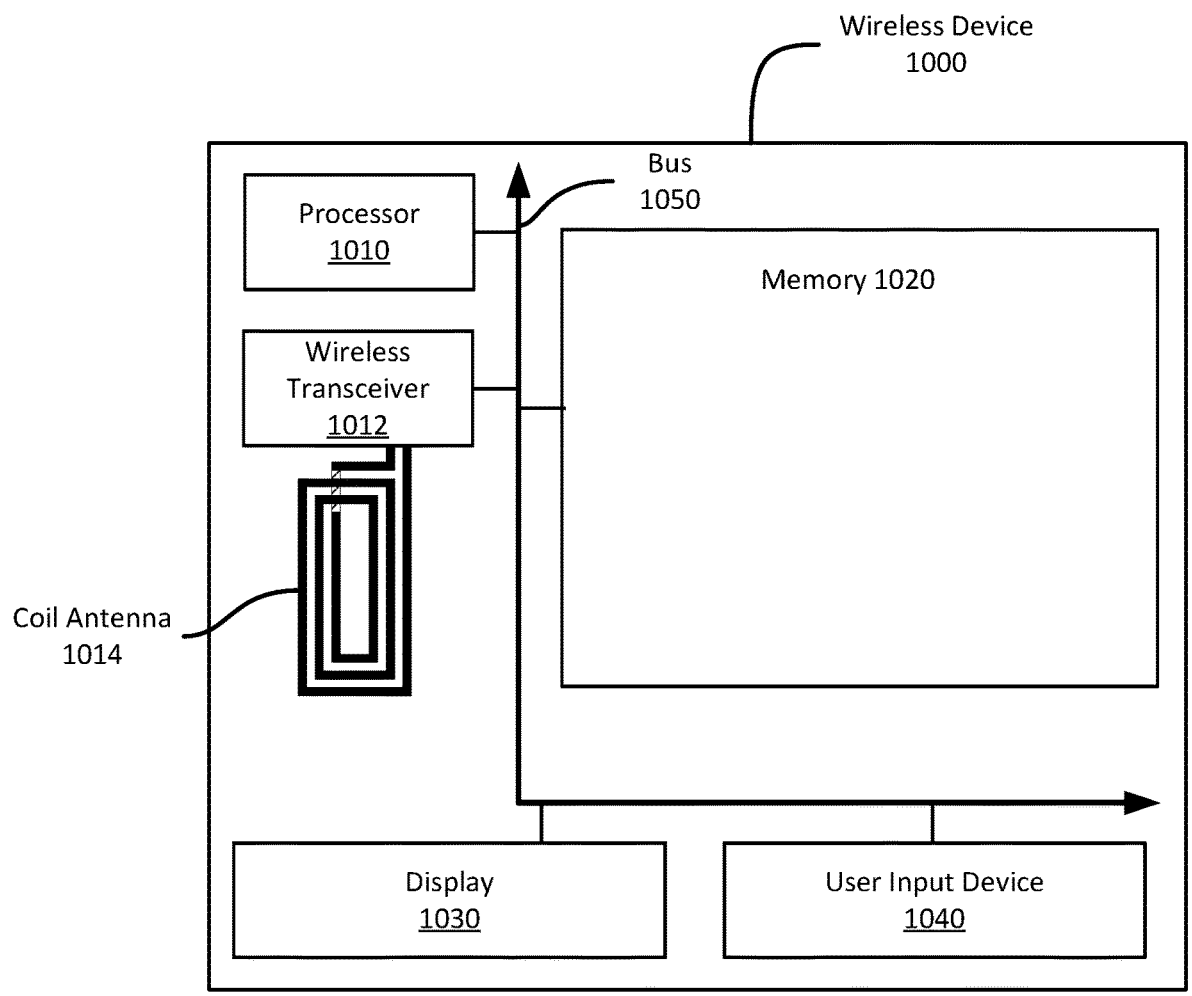
FIG. 10 shows an example wireless computing device.

Referring now to FIG. 10, FIG. 10 shows an example computing device 1000. In the example shown in FIG. 10, the computing device includes a processor 1010, a memory 1020, a wireless transceiver 1012, a display 1030, a user input device 1040, and a bus 1050. In this example, the computing device 1000 comprises a cellular smartphone, but may be any suitable computing device, include a cellular phone, a laptop computer, a tablet, a phablet, a personal digital assistant (PDA), wearable device, etc. The processor 1010 is configured to employ bus 1050 to execute program code stored in memory 1020, to output display signals to a display 1030, and to receive input from the user input module 1040. In addition, the processor 1010 is configured to transmit information to the wireless transceiver 1012. The wireless transceiver 1012 is configured to transmit and receive wireless signals via coil antenna 1014. For example, the wireless transceiver 1012 may be configured to generate an EMF to electromagnetically couple the coil antenna 1014 with another coil antenna, such as may incorporated into any of the devices described above.

While some examples of methods and systems herein are described in terms of software executing on various machines, the methods and systems may also be implemented as specifically-configured hardware, such as field-programmable gate array ("FPGA") specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory ("RAM") coupled to the processor. The processor executes computer-executable program instructions stored in memory, such as executing one or more computer programs. Such processors may comprise a microprocessor, a digital signal processor ("DSP"), an application-specific integrated circuit ("ASIC"), field programmable gate arrays, and state machines. Such processors may further comprise programmable electronic devices such as programmable logic controllers ("PLCs"), programmable interrupt controllers ("PICs"), programmable logic devices ("PLDs"), programmable read-only memories ("PROMs"), electronically programmable read-only memories ("EPROMs" or "EEPROMs"), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A system comprising:
 a biosensor applicator comprising:
  a housing defining a cavity configured to receive and physically couple to a biosensor device, and to apply the biosensor device to a wearer;
  a first applicator coil antenna physically coupled to the biosensor applicator and defined within a first plane; and
  a second applicator coil antenna physically coupled to the biosensor applicator and defined within a second plane substantially parallel to and different from the first plane, the second applicator coil antenna positioned substantially coaxially with respect to the first applicator coil antenna,
  wherein the first applicator coil antenna is configured to wirelessly receive electromagnetic ("EM") energy from a transmitter coil antenna of a remote device and provide at least a first portion of the received EM energy to the second applicator coil antenna; and
 a biosensor device comprising:
  a biosensor coil antenna defined within a third plane substantially parallel to and different than the first and second planes;
  a wireless receiver electrically coupled to the biosensor coil antenna;

wherein the biosensor device is physically coupled to the biosensor applicator and positioned within the cavity;

wherein the biosensor coil antenna is positioned and oriented substantially coaxially with respect to the second applicator coil antenna, and wherein the second applicator coil antenna is configured to receive EM energy from the first applicator coil antenna and wirelessly transmit at least a second portion of the received EM energy to the biosensor coil antenna.

2. The system of claim 1, wherein the first applicator coil antenna is configured to wirelessly transmit the first portion of such received EM energy to the second applicator coil antenna.

3. The system of claim 1, further comprising an electrical conductor coupled between the first applicator coil antenna and the second applicator coil antenna to electrically couple the first and second applicator coil antennas.

4. A biosensor applicator device comprising:

a biosensor applicator housing configured to receive and physically couple to a biosensor device, the biosensor applicator configured to apply the biosensor device to a wearer;

a first coil antenna physically coupled to the biosensor applicator; and a second coil antenna physically coupled to the biosensor applicator, the second coil antenna located distant from the first coil antenna and substantially co-axially aligned with the first coil antenna, and wherein the first coil antenna is configured to:

wirelessly receive electromagnetic ("EM") energy from a transmitter coil antenna; and provide at least a portion of the received EM energy to the second coil antenna.

5. The biosensor applicator device of claim 4, further comprising an electrical conductor physically coupled between the first and second coil antennas, the electrical conductor electrically coupling the first and second coil antennas, and wherein the first coil antenna is configured to provide the received EM energy to the second coil antenna by transmitting the received EM energy to the second coil antenna using the electrical conductor.

6. The biosensor applicator device of claim 4, wherein:

the first coil antenna is substantially electrically insulated from the second coil antenna; and wherein the first coil antenna is configured to provide the received EM energy to the second coil antenna by wirelessly transmitting the received EM energy to the second coil antenna.

7. The biosensor applicator device of claim 4, wherein a distance from the first coil antenna to the second coil antenna is less than or equal to substantially twice the width of the first coil antenna.

8. The biosensor applicator device of claim 4, wherein the second coil antenna is configured to wirelessly transmit the received EM energy to a biosensor coil antenna of a biosensor device.

9. The biosensor applicator device of claim 7, wherein the biosensor device is a continuous glucose monitor.

10. The biosensor applicator device of claim 4, wherein the first coil antenna is substantially planar.

11. The biosensor applicator device of claim 4, wherein the first coil antenna is substantially helical.

12. A biosensor applicator comprising:

a biosensor applicator housing configured to receive and physically couple to a biosensor device, the biosensor applicator configured to apply the biosensor device to a wearer;

a first coil antenna;

wherein the first coil antenna is configured to:

wirelessly and electromagnetically couple with a transmitter coil antenna to receive electromagnetic ("EM") energy from the transmitter coil antenna, and wirelessly and electromagnetically couple with a biosensor coil antenna of a biosensor device to relay at least a portion of the received EM energy to the biosensor coil antenna.

13. The biosensor applicator of claim 12, wherein the first coil antenna is substantially planar.

14. The biosensor applicator of claim 12, wherein the first coil antenna is substantially helical.

15. The biosensor applicator of claim 12, wherein a width of the first coil antenna is configured to be equal to at least half a distance between the first coil antenna and a remote coil antenna, the remote coil antenna being part of the biosensor applicator or being the biosensor coil antenna when the biosensor device is installed in the biosensor applicator.

16. The biosensor applicator of claim 12, wherein the biosensor device is physically coupled to the biosensor applicator.

17. The biosensor applicator of claim 16, wherein the biosensor device is a continuous glucose monitor.

18. A method comprising:

generating, using an electronic device, an alternating electromagnetic field ("EMF"), the electronic device comprising a wireless transmitter and a transmitter coil antenna, the wireless transmitter electrically coupled to the wireless transmitter;

receiving, by a first coil antenna of a biosensor applicator, energy from the alternating EMF, wherein the biosensor applicator comprises:

the first coil antenna; and a second coil antenna, the second coil antenna located distant from and substantially co-axially aligned with the first coil antenna;

transmitting, by the first coil antenna, energy received from the alternating EMF to the second coil antenna;

transmitting, by the second coil antenna, energy received from the first coil antenna to a biosensor coil antenna of a biosensor device, wherein the biosensor device comprises the biosensor coil antenna and a wireless receiver, the biosensor coil antenna electrically coupled to the wireless receiver.

19. The method of claim 18, further comprising activating the biosensor device using the alternating EMF.

20. The method of claim 18, further comprising providing power to the biosensor device using the alternating EMF.

21. The method of claim 18, further comprising obtaining data from the biosensor device using the alternating EMF.

22. The method of claim 18, wherein the first coil antenna is electrically coupled to the second coil antenna by an electrical conductor, and wherein transmitting the received energy from the EMF from the first coil antenna to the second coil antenna uses the electrical conductor.

23. The method of claim 22, wherein the biosensor device is physically coupled to the biosensor applicator.

24. The method of claim 23, wherein the biosensor device is a continuous glucose monitor.

25. The method of claim 18, wherein the first coil antenna is electrically insulated from the second coil antenna.

26. A method comprising:
generating, using an electronic device, an alternating electromagnetic field ("EMF"), the electronic device comprising a wireless transmitter and a transmitter coil antenna electrically coupled to the wireless transmitter;
wirelessly and electromagnetically coupling, by a first coil antenna of a biosensor applicator, with the transmitter coil antenna to receive energy from the alternating EMF, the biosensor applicator comprising the first coil antenna; and
wirelessly and electromagnetically coupling, by the first coil antenna, with a biosensor coil antenna of a biosensor device to relay at least a portion of the energy received from the alternating EMF.

27. The method of claim 26, further comprising activating the biosensor device using the relayed energy from the alternating EMF.

28. The method of claim 26, further comprising providing power to the biosensor device using the alternating EMF.

29. The method of claim 26, further comprising obtaining data from the biosensor device using the alternating EMF.

30. The method of claim 26, wherein the biosensor device is physically coupled to the biosensor applicator.

31. The method of claim 30, wherein the biosensor device is a continuous glucose monitor.

* * * * *